United States Patent [19]

Rouet

[11] 4,389,576
[45] Jun. 21, 1983

[54] INSTALLATION TO MEASURE THE VISIBILITY LIMIT IN A FOG

[76] Inventor: Paul Rouet, Avenue Meurée, 4, B 6001 Marcinelle, Belgium

[21] Appl. No.: 282,786
[22] Filed: Jul. 13, 1981

[30] Foreign Application Priority Data

Jul. 17, 1980 [EP] European Pat. Off. ............ 80200696

[51] Int. Cl.³ .......................................... G01M 15/06
[52] U.S. Cl. .................................... 250/573; 356/438
[58] Field of Search ................ 250/573, 575; 356/438, 356/439

[56] References Cited
FOREIGN PATENT DOCUMENTS 1459336 10/1965 France .

Primary Examiner—David C. Nelms
Assistant Examiner—Darwin R. Hostetter
Attorney, Agent, or Firm—Schwartz, Jeffery, Schwaab, Mack, Blumenthal & Koch

[57] ABSTRACT

Installation to measure the limit of visibility in a fog, comprising a motor of a control device effecting the setting of the variable focus of the optical apparatus (1) and simultaneously driving one or several moving assemblies (8) displaceable with respect to one or several stationary assemblies (9). In each combination of a moving assembly (8) and the corresponding stationary assembly (9), one of the two assemblies comprises at least one detector (11) or sensor (12) of numerical and/or analog information consigned to the other assembly and having as its object the light of the series of lights upon which the variable focus is set.

7 Claims, 3 Drawing Figures

INSTALLATION TO MEASURE THE VISIBILITY LIMIT IN A FOG

BACKGROUND OF THE INVENTION

In French Pat. Nos. 1 459 336 and 94472/1 459 336 there is described an installation to measure the distance limiting visibility in a fog, comprising a series of lights disposed for example along a landing strip of an airfield or another measuring area, an optical observation device projecting the image of one or a plurality of lights of the series onto an observation screen, for example the target of a television imaging tube or one of a plurality of photoelectric cells and a motorized control device to set the variable focal lens of the optical device on a selected light of said series and to simultaneously actuate the lights viewed on the optical device. The lights may be illuminated continuously or in a blinking manner.

SUMMARY OF THE INVENTION

It is the object of the invention to improve the known installation so as to increase its reliability and performance.

The installation according to the invention is characterized in that the motor of the control device, effecting the setting of the variable focal lens of the optical apparatus, simultaneously entrains one or more mobile assemblies which are displaced with respect to one or more stationary assemblies. In each combination, of the mobile assembly and the corresponding stationary assembly, one of the two assemblies compries at least one detector or sensor of numerical and/or analog information projected onto the other of the two assemblies and has as its object the light of the series of lights upon which the variable focal lens is set. This numerical and-/or analog information may relate specifically to the control of the actuation of certain lights of the series, for example to the actuation of the light upon which the variable focal lens is set, to the choice of a perception or detection threshold as a function of the setting of the variable focal length, to the transmission of the display of the visibility distance limit, if the light upon which the variable focal length is set is located at the limit of visibility, or to the orientation of the optical device to center the image of the light upon which the focal length is set on a specific, predetermined point on the screen or the target of a photoelectric detector and also to the motion of the motor when the focussing of the focal lens on one of the lights is terminated.

The equipment according to the invention comprises preferably an automatic apparatus consisting of a detector of visibility with respect to a threshold, one or several illuminated lights, controlling the actuation of the motor to adjust the variable focal length to a light located closer if it senses the absence of visibility and to a farther light, if visibility is good, and to actuate the display of the limit distance of visibility, if it determines that the limit has been attained.

In order to facilitate this measure of visibility, the light actuated, or the lights actuated for the measurement are preferably blinking at a frequency appreciably lower than the frequency of the alternating feed current of the lights. This will serve to distinguish them from a beacon light or any kind of stationary or moving light, without the possibility of error.

BRIEF DESCRIPTION OF THE DRAWINGS

The invention shall be explained hereinbelow in relation to two embodiments and with reference to the drawing attached hereto, wherein.

DETAILED DESCRIPTION OF THE DRAWINGS

Figure 1:
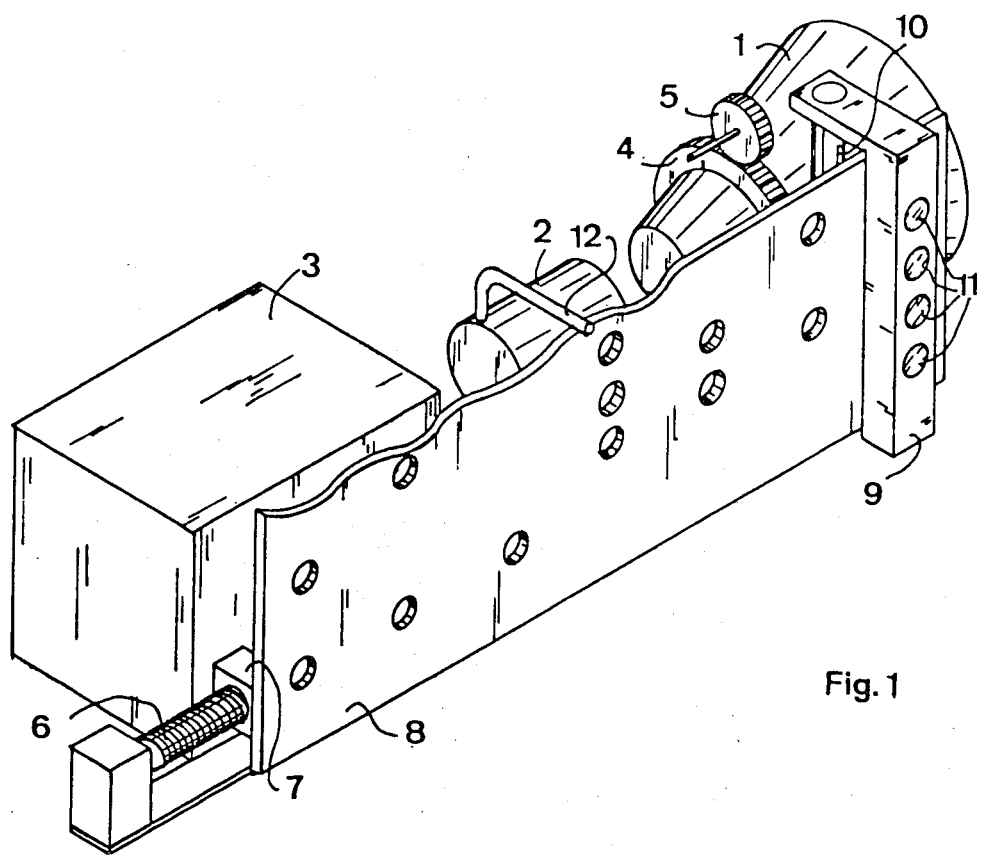
FIG. 1 is a perspective view of an optical apparatus according to the present invention.

In FIG. 1, an optical device directed at a series of lights, not shown, is equipped with 1 a variable focal length "ZOOM" lens and mobile optical assembly 2, making it possible to center the image of the light on a predetermined point of a screen or the target of a photoelectric detector, housed in a box 3. The variable focal length assembly 1 carries a rack 4 operated by a pinion 5 of a motor, not shown, which also drives, by way of the rack 4 and the gears, not shown, a mobile assembly consisting of a leadscrew 6 and a nut 7. The nut 7 may be integral with a metal plate 8, which moves across or in front of a stationary assembly 9 in the form of a yoke, supporting a strip of lights 10 on one side of the plate and an assembly 11 of several detectors on the other side of the plate. The holes provided in the plate 8, facing the detectors 11, are representative of the numerical information that may be determined by the detectors 11 and may be connected for example with the settings of the variable focus on certain lights of the series and the controls of the electronic measuring circuit.

A specific shape of the upper edge of the plate 8 permits the transmission of analog information as a function of the setting of the mobile optical assembly 2, making possible the centering of the light of the series upon which the variable focus is set.

Several variants are possible. Different information may be consigned to different assemblies. Instead of the metal plate 8, the yoke 9 may be displaced. In place of optoelectric detection by transparency, a detection of reflecting plates may be envisioned, or magnetic detection may be provided by equipping, for example, the plate 8 with magnetic tablets. Instead of moving a rigid plate 8, it may be replaced by one or several flexible films stretched over drums, one of which is moving and is entrained simultaneously with the rack 4. The flexible film or films may be opaque, for example metallic, or transparent and coated with an opaque layer. In these two cases, the films are provided with holes or reflecting platelets representing numerical or analog information.

Figure 2:
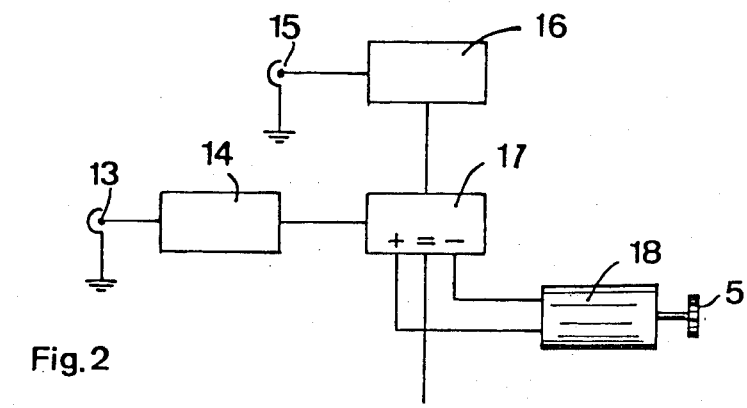
FIG. 2 is a schematic of one embodiment of a control for the optical apparatus.

FIG. 2 shows a block diagram of an automatic equipment. The target of a photoelectric tube 13 receives the ambient light. The tube 13 thus functions as a detector of ambient luminosity and affects a threshold generator 14. On the other hand, the target of another photoelectric tube 15 receives the blinking light of a light upon which the optical device is set. This blinking is preferably due to modulation of the light current by a constant frequency that is predetermined, for example, 31, 27 or 22 Hz, if the frequency of the alternating current is 50 Hz. The frequency may vary from one light to the other. The output signal of the photoelectric tube 15 is passed to a detector 16 of the blinking luminosity of the lights of the series of lights placed along the measuring site. If the blinking takes place at a precise, constant frequency, the detector 16 may consist of a synchronous detector, potentially adaptable to the proper frequency of each light. The output of the detector 16 on the one hand, and of the threshold generator 14 on the other, are applied to a comparator 17 which has a + outlet, a = outlet and a − outlet, and is connected on one side with a motor 18 moving the pinion 5 and on the other, with a display device, not shown. The comparator 17 may consist of a simple electronic device, or a microcomputer performing controls more complex than those described hereinabove, by placing certain data in the memory of the microcomputer permitting the elimination of specific causes of error or the transmission of the results of the measurements by a synthesized voice, etc.

When the blinking luminosity is well visible in relation to the threshold of ambient luminosity, a pulse appears at the outlet and actuates the motor 18 in the direction of setting the variable focus on a light farther away. If, in contrast, the blinking light is not perceptible with respect to the threshold of the ambient luminosity, a pulse appearing at the − outlet actuates the motor 18 in the direction of setting the variable focus device 1 on a light located closer to the apparatus. In both cases, the motor 18 is stopped when the setting of the apparatus on the next light is completed and remains at rest during the measuring period. When the blinking luminosity is at the limit of visibility, the motor 18 is no longer actuated, but a pulse from the = outlet is transmitted to a device displaying the limit distance of the visibility in the fog. The value measured may be transmitted in any form whatsoever: the illumination of prepared lettering, illumination of a panel of visible lights, the broadcasting of a synthetic voice or of prerecorded phrases, etc.

In order to provide protection against different errors, for example the failure of one or several of the lights, an error due to the hiding of a light by a moving or stationary obstacle or an error introduced by a small fog bank obscuring one or two of the lights partially or totally, while leaving the other lights of the series free, it is advantageous to provide a periodic systematic inspection of the entire series of lights, for example by lighting one lamp at a time and committing the number of lamps lit to the memory. At such time, it is also possible, by eliminating the intervention of the threshold of perception, to determine by means of the measuring apparatus, the existence of lamps which are more visible to an observer or a pilot.

It is also possible to use only a single photoelectric detector and thereby measure on the one hand the direct components of the light and on the other, an alternating component due to the modulating frequencies. The direct component is applied to the threshold generator 14 and the alternating component to the detector 16.

Figure 3:
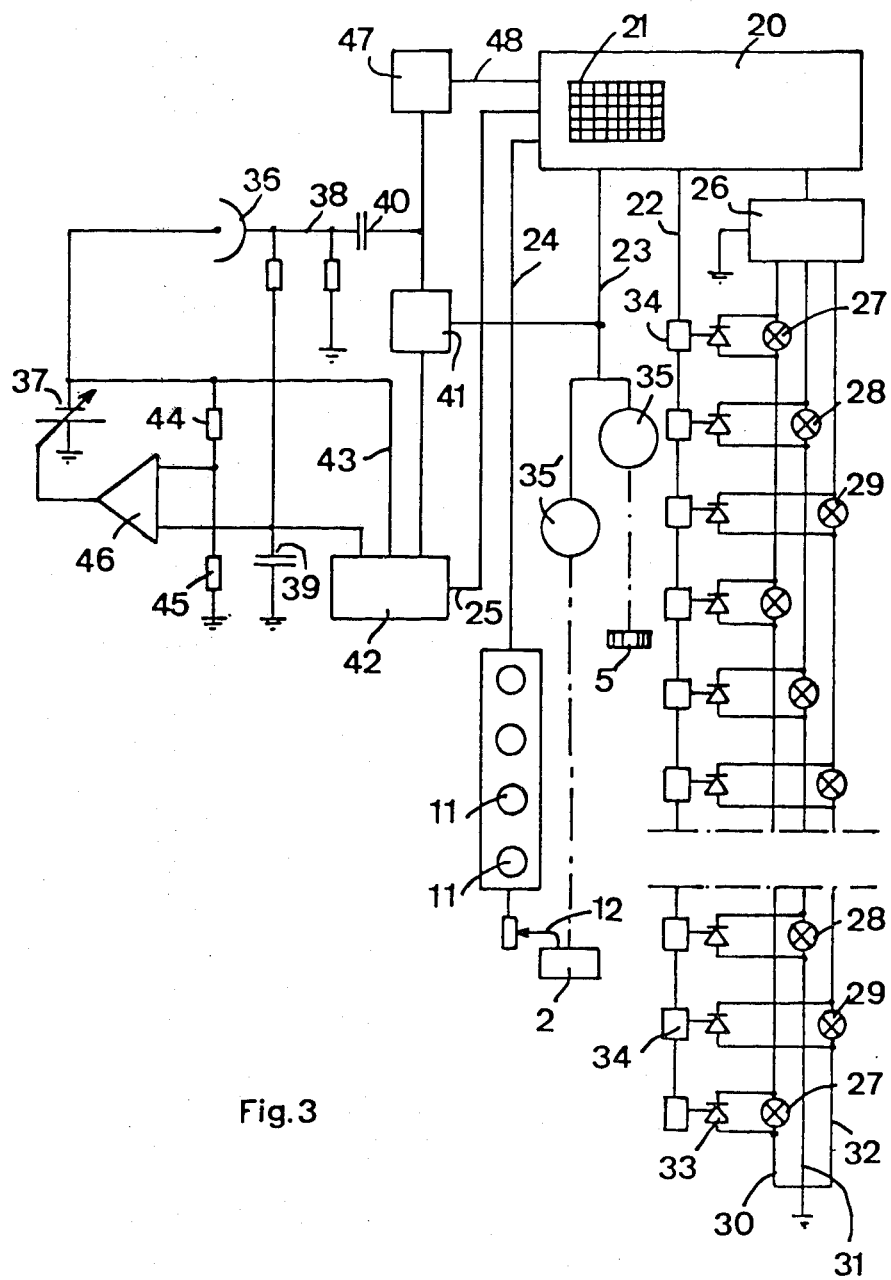
FIG. 3 is a schematic of a second embodiment of a control for the optical apparatus.

FIG. 3 shows a complete control diagram. A computer 20 has a manual control panel 21 and several outlets 22, 23 and inlets 24, 25. The manual control panel offers a choice of an automatic or of a completely manual operation. The latter ressembles the operation already described in FR Nos. 1 459 336 and 94472/1 459 336 and will not be explained here. A source of power 26 permits the lighting of the lamps 27, 28, 29 of a series of lights placed along a measuring distance, on the ground. The lamps of the series of lights may all be supplied at the same flashing frequency, which is sufficient if a single light is actuated at a time. If, in contrast, it is desired to light for example three lights at a time, the power source 26 contains not one but three power outlets, each for a different lighting frequency, for example 31, 27 and 22 Hz. The consecutive lights of the series along the measuring distance are each connected to a series circuit 30, 31, 32, in turn connected with one of the three power outlets. Each light is placed in parallel with a commutation device 33. In each of the circuits 30, 31, 32, all of the lights except one are short-circuited by the devices 33. The lights are actuated by means of an order issued over an outlet 22, which may consist of a single conductor or an assembly of n conductors, n being the number of lights in the series. These orders are processed in the computer 20 as a function of the signals emitted by the detectors 11, which in turn indicate the position of the moving assembly 8 (FIG. 1). The data provided by the detectors 11 are supplied to the computer through the inlet 24. The outlet 22 is connected with the control means 34 of the commutating devices 33. By actuating three lights at a time, by means of rendering three devices 33 blocking, one in each of the circuits 30, 31, 32, a single light is actuated in each of the circuits, so that each of the lamps lit flashes at a different frequency.

The computer 20 also issues, for example on the outlet 23, displacement instructions for the coarse positioning of the optical device and specifically for the setting of its variable focus. The outlet 23 is considered herein as a multiple outlet, capable of controlling a motor 35 driving the pinion 5 and possibly other servomotors modifying the orientation of an object, not shown, or the motor 35' controlling the orientation of the assembly 2, if the arm 12 does not actuate the assembly 2 directly, but is acting as a control voltage selector, for example.

A photometric cell 36, which may also be a photon multiplier, is normally located in the box 3 shown in FIG. 1. It is supplied by a feed voltage from a source 37, represented for the sake of simplicity by a battery.

When the target of the cell 36 is impacted by an image of a flashing light on a background of ambient luminosity, the output signal collected at the anode 38 of the cell 36 consists of a direct component appearing on the terminals of a capacitor 39 and an alternating component passing through a capacitor 40. The alternating component enters a peak voltage detector 41, the sensitivity of which is controlled by an order issued through the outlet 23 of the computer 20 as a function of the light actuated, the visibility of which is to be measured. The detector 41 may thus be rendered sensitive, in turn, in frequency and in phase to the luminosities generated by one of the lights connected with one of the power outlets 30, 31, 32 of the source 26. In this manner, the light emitted by the other lights does not affect the measurement of the light to which the detector is sensitive. The output voltage of the detector 41 is applied to a decision circuit 42, wherein it is compared with a voltage which is a function of the direct component of the output signal of the cell 36 that is appearing at the terminals of the capacitor 39. The decision circuit 42 may include a threshold generator, thereby providing at its outlet a logic signal representing the visible or invisible condition of the light involved. This signal is introduced in the computer 20 through the inlet 25.

As the ambient luminosity in a fog may easily vary by a factor of $10^4$ between dusk and full daylight and since the eye is more sensitive to small differences in luminosity in twilight than in daylight, the decision circuit 42 must be combined with a visibility threshold generator operating as a function of a signal proportional to the ambient luminosity. Such a signal consists, for example, of the voltage appearing on the terminals of the capacitor 39, i.e. the direct component of the output signal of the cell 36. It is advantageous to keep the threshold generator very simple and to account for the great variability of the ambient lumninosity by adapted means, for example by measuring the alternating component due to the flashing of a light, determined in the part of the characteristic of the response of the cell 36, which is close to the saturation level, as described hereinbelow. Thus, the circuit 42, in the most favorable case, is merely a discriminator of the voltage proportional to the alternating component passing through the capacitor 40 with respect to a constant fraction of the direct component on the terminals of the capacitor 39. As a general rule, however, the ideal case is not attained and the comparison is effected with respect to a fraction of the direct component, which varies according to the absolute value of the ambient luminosity, determined for example by measuring the feed voltage of the source 37, introduced in the circuit 42 by means of a conductor 43. A circuit to select the operating point on the response characteristic of the cell 36, making it possible to choose this point with respect to and close to the saturation level of this characteristic, is described hereinbelow. The voltage of the source 37 supplying the cell 36 is variable and is maintained constantly at a level such that the direct component generated by the level of ambient luminosity is slightly less than the saturation level of the cell 36, for example 95% of this value. A suitable circuit capable of performing this function consists for example of a voltage divider 44, 45 and a servoamplifier 46, the output of which adjusts the value of the voltage of the source 37. The output of 46 is a function of a difference voltage between the voltage provided by the voltage divider 44, 45 and the direct component of of the output signal of the cell 36, appearing on the terminals of the capacitor 39 applied to the inlet of the servoamplifier 46.

Even in the case of a single lamp lit and more so with a plurality of lamps actuated simultaneously, an exaggerated saturation of the cell 36 may take place. This may be discovered in a suitable detector 47, the outlet of which furnishes a signal to an inlet 48 of the computer. The latter can then either impose slower frequencies on the source 26, or interrupt instantaneously the actuation of all of the lamps except one, in order to verify whether the exaggerated saturation originates in the lights of the measuring distance or in other causes.

I claim:

1. An apparatus for measuring the limit distance of visibility in a fog, comprising
   a series of lights placed along a measuring distance;
   an observation screen;
   optical apparatus having a variable focus means for projecting an image of one or more of said lights on said observation screen;
   control means for setting said variable focus means on a light selected from said series of lights and simultaneously actuating said selected light;
   at least one stationary assembly;
   at least one movable assembly which moves in relation to said stationary assembly;
   wherein one of said movable and stationary assemblies includes detectable information and the other of said movable and stationary assemblies includes at least one detector for detecting said information; and wherein said control means drives said movable assembly simultaneously with setting of said variable focus means whereby the position of said movable assembly indicates the positioning of said variable focus means.

2. The apparatus according to claim 1 wherein said control means includes a threshold generator producing a signal indicative of the ambient luminosity, a device to measure the luminosity of said selected light, and a comparator responsive to said threshold generator and said device, said comparator producing an output for effecting the setting of said variable focus means.

3. The apparatus according to claim 2 wherein said control means further includes means for flashing each of the lights of said series at a different frequency, and wherein said device to measure luminosity comprises a synchronous detector which can be adapted to the frequency of each light of said series.

4. The apparatus according to claim 1 wherein said control means comprises means for producing a signal indicative of visibility, a computer for receiving said signal indicative of visibility, and at least one servomotor responsive to said computer for adjusting said variable focus means.

5. The apparatus according to claim 2 wherein said control means includes a photometric cell, and wherein said threshold generator comprises circuit means for the selection of the operating point of said photometric cell.

6. An apparatus according to claim 5 wherein said selection circuit means comprises a voltage divider, said voltage divider dividing the feed voltage of said photometric cell supplied by a source, and a servoamplifier for controlling the value of said feed voltage as a function of the difference of the deviation between the voltage supplied by the voltage divider and a direct component of the output signal of said photometric cell.

7. The apparatus according to claim 3 wherein said control means includes a plurality of power outlets at different frequencies, each frequency being associated with a different one of said lights of said series, and further wherein said lights are connected in a plurality of series circuits, each of said series circuits being connected to receive one of said frequencies, and a commutating device associated with each of said lights for short circuiting the associated light whereby all lights in one series circuit except one can be short circuited.

* * * * *